(12) United States Patent
Sim et al.

(10) Patent No.: US 9,751,910 B2
(45) Date of Patent: Sep. 5, 2017

(54) METHOD FOR PREPARING METAL NANOSTRUCTURE BASED ON BIOMOLECULES

(71) Applicant: KOREA UNIVERSITY RESEARCH AND BUSINESS FOUNDATION, Seoul (KR)

(72) Inventors: Sang Jun Sim, Seoul (KR); Xingyi Ma, Seoul (KR); Jong-Uk Lee, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 14/898,741

(22) PCT Filed: Jul. 3, 2014

(86) PCT No.: PCT/KR2014/005959
§ 371 (c)(1),
(2) Date: Dec. 15, 2015

(87) PCT Pub. No.: WO2015/023059
PCT Pub. Date: Feb. 19, 2015

(65) Prior Publication Data
US 2016/0137687 A1 May 19, 2016

(30) Foreign Application Priority Data
Aug. 13, 2013 (KR) .................... 10-2013-0095688

(51) Int. Cl.
| | | |
|---|---|---|
| C12Q 1/68 | (2006.01) |
| C12M 1/00 | (2006.01) |
| C07H 21/02 | (2006.01) |
| B32B 5/16 | (2006.01) |
| G01N 33/559 | (2006.01) |
| C07H 23/00 | (2006.01) |
| B82B 3/00 | (2006.01) |
| B22F 1/00 | (2006.01) |
| B22F 9/24 | (2006.01) |
| A61K 48/00 | (2006.01) |
| A61K 9/51 | (2006.01) |
| G01N 21/552 | (2014.01) |
| G01N 27/447 | (2006.01) |

(52) U.S. Cl.
CPC ............ *C07H 23/00* (2013.01); *A61K 9/5115* (2013.01); *A61K 9/5192* (2013.01); *A61K 48/00* (2013.01); *B22F 1/0018* (2013.01); *B22F 1/0062* (2013.01); *B22F 9/24* (2013.01); *B82B 3/0033* (2013.01); *G01N 21/554* (2013.01); *G01N 27/44747* (2013.01); *C22C 2202/02* (2013.01)

(58) Field of Classification Search
CPC ........ C12C 1/68; B82B 3/0033; G01N 21/54; C40B 30/04
USPC ........... 435/6.1, 7.1, 283.1, 287.2; 536/23.1; 977/702, 773; 428/402; 204/456
See application file for complete search history.

(56) References Cited

U.S. PATENT DOCUMENTS

| | | | | |
|---|---|---|---|---|
| 2012/0107242 A1* | 5/2012 | Wang | ................. | A61K 31/7088 424/9.1 |
| 2013/0172207 A1* | 7/2013 | Dai | ...................... | G01N 33/553 506/9 |
| 2013/0330839 A1 | 12/2013 | Suh et al. | | |

FOREIGN PATENT DOCUMENTS

| | | |
|---|---|---|
| EP | 2511231 A2 | 10/2012 |
| KR | 1020120096120 A | 8/2012 |
| KR | 1020130065159 A | 6/2013 |
| WO | 2013006411 A1 | 1/2013 |

OTHER PUBLICATIONS

Zhang et al, pH induced protein-scaffold biosynthesis of tunable shape gold nanoparticles, 2011, Nanotechnology, 22, 355603, 9 pages.*
Demers et al, Thermal Desorption Behavior and Binding Properties of DNA Bases and Nucleosides on Gold, 2002, JACS, 124, 11248-11249.*
Ma et al (post art), Gold nanocrystals with DNA-directed morphologies, Nature communications, 2016, 7, 12873, 8 pages.*
Kundu, S., et al., "The self-assembling of DNA-templated Au nanoparticles into nanowires and their enhanced SERS and catalytic applications", RSC Advances, Jul. 2, 2013, pp. 16486-16498, vol. 3.
Zahn, Z., et al., "Gold-based optical biosensor for single-mismatched DNA detection using salt-induced hybridization", Biosensors and Bioelectronics, Dec. 6, 2011, pp. 127-132, vol. 32.
Zongrui, Z., "Development of DNA biosensor based on the optical properties of gold nanoparticles", "Master's Thesis for the Graduate School, Sungkyunkwan University, Department of Chemical Engineering", Dec. 2010, pp. 1-79.

* cited by examiner

Primary Examiner — Narayan Bhat
(74) Attorney, Agent, or Firm — Hultquist, PLLC; Steven J. Hultquist

(57) ABSTRACT

The present invention relates to a method for preparing metal nanostructures using DNA, and more particularly, to a method for preparing metal nanostructures, in which a self-assembling DNA is used as a frame, and thus the orientation, shape and size of the nanostructures are easily controlled compared to conventional bottom-up methods. Metal nanostructures prepared by the method show excellent localized surface plasmon resonance properties, and thus can be used as fluorescent substances in drug delivery, biomedical imaging, and supersensitive biosensors.

11 Claims, 7 Drawing Sheets

5 second　　　　　15 second　　　　　30 second

FIG. 6
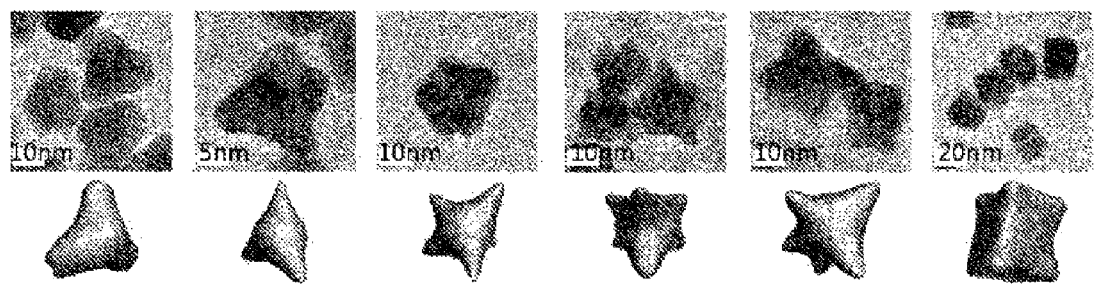
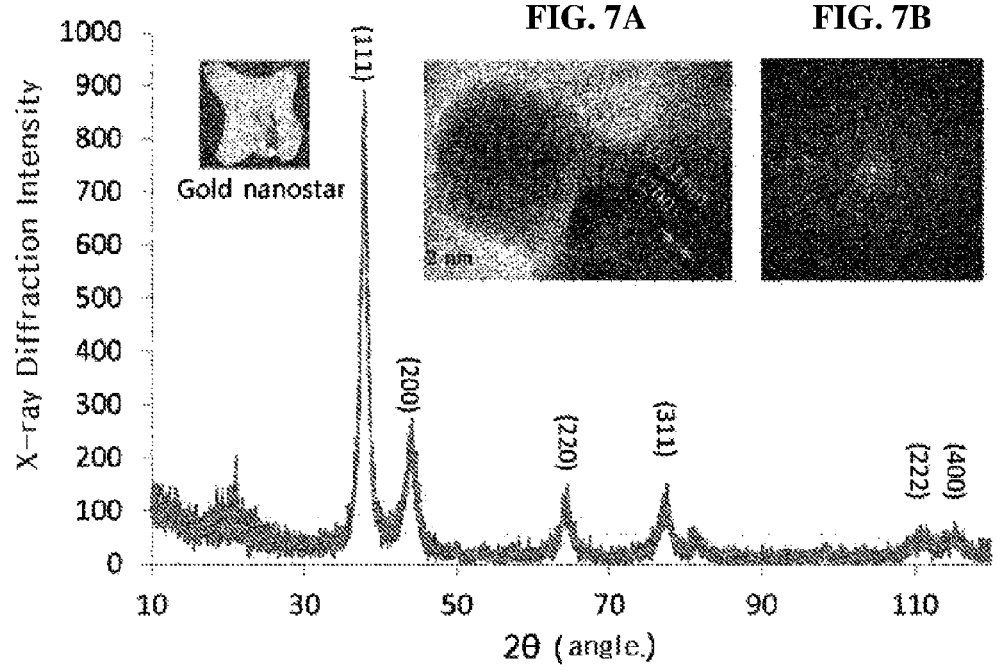
FIG. 7A    FIG. 7B

FIG. 8
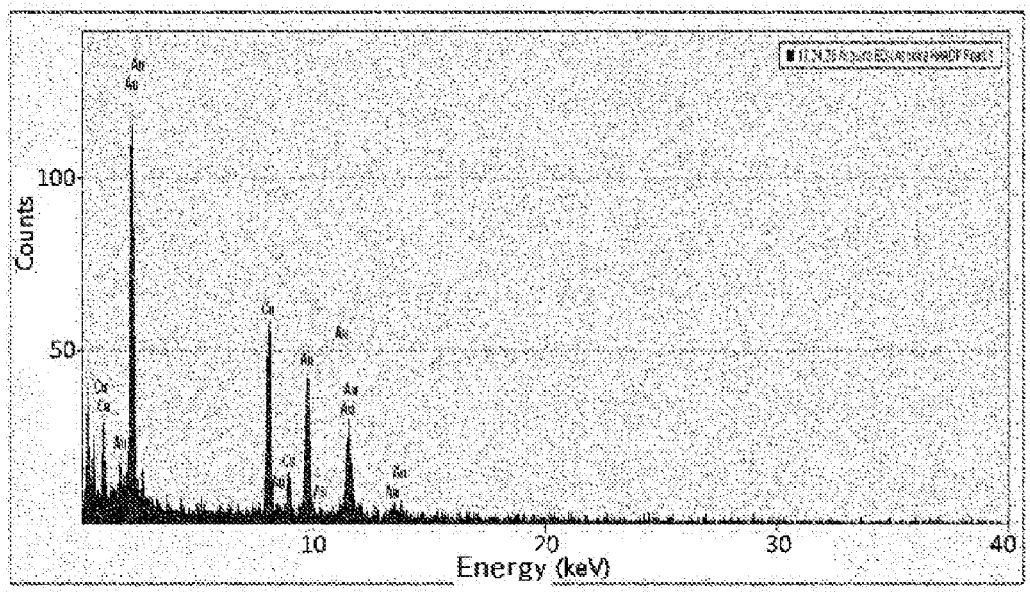
FIG. 9A  FIG. 9B  FIG. 9C
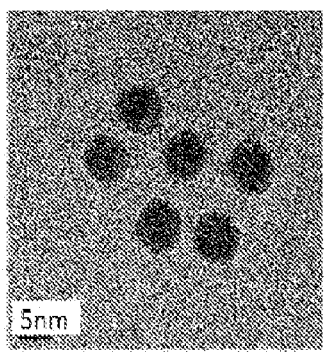 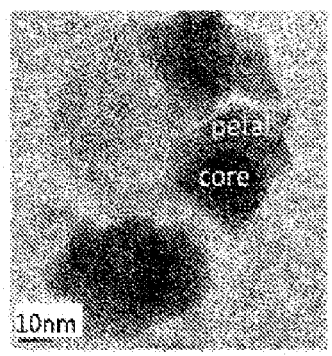 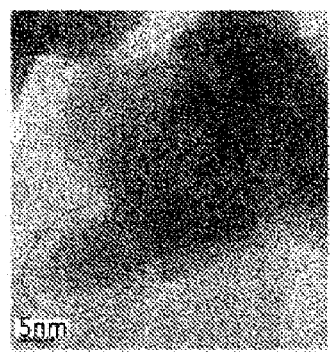

METHOD FOR PREPARING METAL NANOSTRUCTURE BASED ON BIOMOLECULES

CROSS-REFERENCE TO RELATED APPLICATIONS

This application is a U.S. national phase under the provisions of 35 U.S.C. §371 of International Patent Application No. PCT/KR14/05959 filed Jul. 3, 2014, which in turn claims priority of Korean Patent Application No. 10-2013-0095688 filed Aug. 13, 2013. The disclosures of such international patent application and Korean priority patent application are hereby incorporated herein by reference in their respective entireties, for all purposes.

TECHNICAL FIELD

The present invention relates to a method for preparing biomolecule-based metal nanostructures, and more particularly, to a method of preparing metal nanostructures, the orientation, shape and size of which are controllable, by use of self-assembling biomolecules.

BACKGROUND ART

Nanoparticles have unique properties (for example, optical, electromagnetic and catalytic properties, etc.) that are completely different from bulk properties. The reason why nanoparticles have such properties is because the nanoparticles have an increased specific surface area which results in a change in the properties. In metal nanoparticles, a localized surface plasmon resonance (LSPR) phenomenon is observed. The intensity or frequency of the absorption band of metal nanoparticles differs depending on the kind of metal nanoparticles and the kind of material on which nanoparticles are placed. Further, the surface plasmon frequency of metal nanoparticles differs depending on the size, shape and size distribution thereof.

Methods for preparing such nanoparticles can be divided into a top-down method and a bottom-up method. The top-down method is a process that sculpts a mass to make it small. This method has a limit to miniaturization, because it cannot prepare a material having a size of 50 nm or less. The bottom-up method is a process that prepares a new nanomaterial by combining atoms or molecules, like stacking bricks. Typical examples of the bottom-up method include self-assembly technology. Weak, reversible interactions such as hydrogen bonds, hydrophobic interactions and van der Waals forces act between biomolecules such as DNAs, RNAs and proteins. Such reversible interactions allow biomolecules to spontaneously undergo self-assembly into complex structures, and this phenomenon is called "self-assembly phenomenon". In other words, nanostructures having a size of a few nanometers to a few tens of nanometers can be prepared by assembling biomolecules using this self-assembly phenomenon. However, because the self-assembly phenomenon spontaneously occurs under specific conditions, it is very difficult to delicately control the self-assembly process.

In an attempt to solve this problem, Korean Patent Laid-Open Publication No. 10-2012-0096120 discloses the use of a method of changing reaction conditions (i.e., temperature, pH or salt concentration) to control the self-assembly phenomenon. However, this method has a problem in that, because changes are applied to an aqueous solution of biomolecules, the biomolecules cannot be rapidly controlled.

Therefore, there is a need for continued studies on a method for preparing nanostructures having the same pattern, which can make a desired shape from the initial reaction stage.

DISCLOSURE OF INVENTION

It is an object of the present invention to provide a method for preparing metal nanostructures, which is based on the self-assembly of biomolecules without using a surfactant and which enables the shape and size of the nanostructures to be easily controlled from the initial stage of the preparation process.

Another object of the present invention is to provide metal nanostructures prepared by the above method.

Still another object of the present invention is to provide a localized surface plasmon resonance sensor comprising the metal nanostructures.

To achieve the above objects, the present invention provides a method for preparing a biomolecule-based metal nanostructure, the method comprising the steps of:

(a) forming a self-assembled monomolecular layer of a biomolecule on the surface of a metal nanoseed, thereby forming a metal nanoseed-biomolecule complex; and (b) growing a metal ion on the surface of the complex while reducing the metal ion with a reducing agent.

In an embodiment of the present invention, the metal nanoseed-biomolecule complex may be prepared by the steps of:

(i) binding a desthiobiotin-modified DNA to a streptavidin-modified magnetic particle to form a magnetic particle-DNA complex;

(ii) binding the metal nanoseed to the DNA of the complex to form a magnetic particle-DNA-metal nanoseed complex; and (iii) adding a biotin solution to the magnetic particle-DNA-metal nanoseed complex to separate the bond between the magnetic particle and the DNA and remove the magnetic particle from the complex, thereby obtaining a metal nanoseed-DNA complex, wherein steps (i) to (iii) may be repeatedly performed.

In another embodiment of the present invention, step (i) may further comprise, after forming the magnetic particle-DNA complex, a step of adding the magnetic particle-DNA complex to a mixture solution of EDC and NHS to activate the DNA.

In still another example of the present invention, the metal nanoseed-biomolecule complex may be prepared by the steps of: (i) treating the metal nanoseed surface with an oligonucleotide having a terminal disulfide group and an oligo(ethylene glycol) (OEG-OH) having a hydroxyl group to form a self-assembled monomolecular layer, thereby modifying the metal nanoseed surface; (ii) adding a thiol-terminated DNA to the metal nanoseed, and separating and removing the oligonucleotide from the metal nanoseed by a ligand exchange reaction, thereby preparing a metal nanoseed-DNA complex; and (iii) recovering the metal nanoseed-DNA complex by electrophoresis. Herein, the oligonucleotide may be deoxyadenosine triphosphate (dATP).

In a still another embodiment of the present invention, the metal nanoseed-biomolecule complex may be prepared by the steps of: (i) inserting a DNA intercalating molecule into a plasmid DNA, followed by desalting to obtain a plasmid DNA solution; (ii) adding a metal nanoseed aqueous solution to the plasmid DNA solution to form a metal nanoseed-plasmid DNA complex; and (iii) treating the metal nanoseed-plasmid DNA complex with a buffer (pH 10-14).

In a still another embodiment of the present invention, the DNA intercalating molecule may be 1-pyrenebutyric acid (PBA) or S-(2-[[4-(2-phenanthryl)butyl]amino]ethyl)hydrogen sulfurothioate).

In a still another embodiment of the present invention, the source of the metal ion may be one selected from the group consisting of hydrogen tetrachloroaurate(III) ($HAuCl_4$), sodium tetrachloroaurate(III) ($NaAuCl_4$), gold(III) chloride ($AuCl_3$), and potassium gold(III) chloride ($KAuCl_4$).

In a still another embodiment of the present invention, the reducing agent may be one or more selected from the group consisting of hydroxylamine ($NH_2OH$), sodium diphenylamine sulfonate, ascorbic acid, and poly(allylamine) hydrochloride.

In a still another embodiment of the present invention, the method may further comprise, after step (b), a step of adding MPA to the complex to terminate the growth.

In a still another embodiment of the present invention, the metal nanoseed may be any one selected from the group consisting of nanospheres, nanorods, nanoprisms and nanosheets, and may have a size of 1-100 nm.

In a still another embodiment of the present invention, the metal nanoseed may be made of any one selected from the group consisting of gold (Au), silver (Ag), platinum (Pt), palladium (Pd), copper (Cu), silicon (Si), germanium (Ge), aluminum (Al), and metal oxides.

In a still another embodiment of the present invention, the biomolecule may be any one selected from the group consisting of single-stranded DNAs, double-stranded DNAs, DNA oligomers, RNA oligomers, plasmid DNAs, polypeptides, and proteins, in which the single-stranded DNAs, the double-stranded DNAs, the DNA oligomers and the RNA oligomers may be 5-5,000 by in length, and the plasmid DNAs may be 800-10,000 by in length.

The present invention also provides a biomolecule-based metal nanostructure prepared by the method. Herein, the metal nanostructure may be any one selected from the group consisting of nanospheres, nanorods, nanoprisms and nanosheets, and may have a size of 5-500 nm.

The present invention also provides a localized surface plasmon resonance sensor comprising the metal nanostructure.

BRIEF DESCRIPTION OF THE DRAWINGS

FIG. 6 depicts an HR-TEM image and schematic view of metal nanostructures according to an embodiment of the present invention.

FIG. 7 is the X-ray diffraction spectrum of nanostructures according to an embodiment of the present invention; FIG. 7A is an HR-TEM image; and FIG. 7B is an FFT image.

FIG. 8 is the energy dispersive X-ray spectrum of nanostructures according to an embodiment of the present invention.

FIG. 9 is a schematic view of nanostructures according to an embodiment of the present invention. FIG. 9A is a TEM image of metal nanoseeds, and FIGS. 9B and 9C are TEM images of nanostructures according to an embodiment of the present invention.

BEST MODE FOR CARRYING OUT THE INVENTION

Hereinafter, the present invention will be described in detail.

The present invention relates to a method for preparing biomolecule-based metal nanostructures, and is characterized in that metal nanostructures having a desired size and shape can be prepared from the initial stage of the preparation process by forming a metal nanoseed-biomolecule complex using a certain selected biomolecule and allowing the complex to act as a flame on which a metal ion grows. The present inventors have found the optimum method of forming a metal nanoseed-biomolecule complex by modifying the metal nanoseed surface with a selected biomolecule, and have also observed the presence of metal nanostructures prepared by the method. In addition, it was found that the localized surface plasmon resonance (LSPR) properties of metal nanostructures formed using each biomolecule was significantly improved compared to those of metal nanoseeds.

Methods for controlling the size and shape of the metal nanostructures include the control of the shape of a biomolecule, the control of the number of biomolecules bound to metal nanoseeds, the control of the size of metal nanoseeds, the control of reaction time, the control of the amount of gold ions, the addition of a reaction terminating agent, etc.

(1) Control Based on the Shape of Biomolecule

According to the present invention, a prepared biomolecule is anchored on metal nanoseeds to form a metal nanoseed-biomolecule complex frame, and a gold ions are reduced and the gold atoms crystallize on the frame, thereby preparing metal nanostructures. Herein, the biomolecule may be any one selected from the group consisting of single-stranded DNAs, double-stranded DNAs, DNA oligomers, RNA oligomers, plasmid DNAs, polypeptides, and proteins, and the shape and size of metal nanostructures can be controlled depending on the kind of selected biomolecule.

(2) Control Based on the Number of Biomolecules Bound to Metal Nanoseeds

Figure 3:
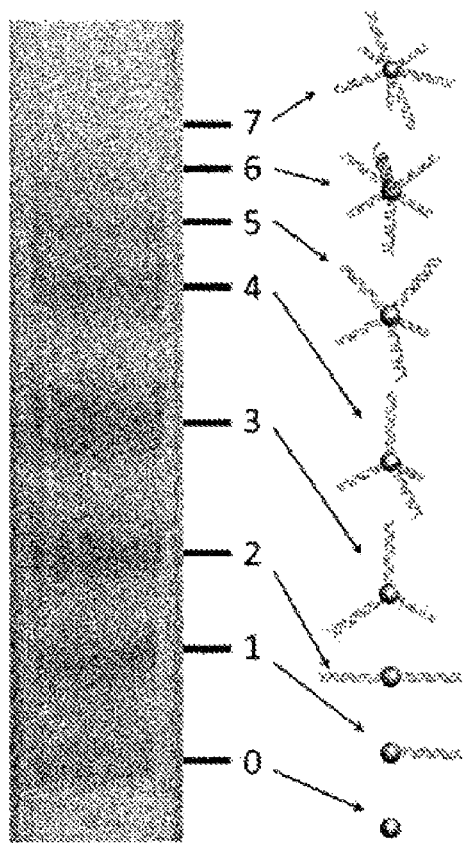
FIG. 3 is a schematic view showing bands obtained from the agarose gel electrophoresis of a metal nanoseed-DNA complex.

The shape of metal nanostructures can also be determined according to the number of biomolecules bound to metal nanoseeds. If the biomolecule is a double-stranded DNA, the number of DNA molecules that can bind to one metal nanoseed may be 1-7. Methods of separating a metal nanoseed-DNA complex include various methods depending on the number of DNA molecules bound. First, if double-stranded DNA is 50-5,000 by in length, the metal nanoseed-DNA complex can be separated by electrophoresis. In this case, as the number of DNA molecules bound to the metal nanoseed increases, the distance of movement in electrophoresis decreases (FIG. 3). Second, if the double-stranded DNA is 50 by or less in length, the metal nanoseed-DNA complex can be separated by a one-after-another approach.

However, in the case of single-stranded DNAs or plasmid DNAs, there is little or no difference in the number of DNA molecules bound to a metal nanoseed. Thus, in this case, it is not required to separate the metal nanoseed-biomolecule complex depending on the number of biomolecules bound to the nanoseed.

(3) In addition to the above methods, the size of metal nanostructures can be controlled depending on the size and shape of a metal nanoseed, the amount of gold ions, the time for growth of gold ions, or the use of a reaction terminating agent. Herein, the metal nanoseed may be any one selected from the group consisting of nanospheres, nanorods, nanoprisms and nanosheets, and may have a size of 1-100 nm. As the reaction terminating agent, mercaptopropionic acid (MPA) may be used.

The metal nanoseed-biomolecule complex is prepared by a self-assembled monomolecular layer on a metal nanoseed using different methods depending on the kind of biomolecule.

A complex of a gold nanoseed and a double-stranded DNA having a short nucleotide sequence can be prepared by a one-after-another approach. Specifically, a first DNA is bound to a gold nanoseed, and second and third DNAs are sequentially bound thereto, thereby controlling the number of DNA molecules forming a self-assembled monomolecular layer on the gold nanoseed.

Furthermore, to prepare a complex of a gold nanoseed and a double-stranded DNA having a short nucleotide sequence, a complex is formed by a ligand exchange reaction with a mononucleotide, and the complex is separated by electrophoresis depending on the number of DNA molecules formed on the gold nanoseed.

In the case of a gold nanoseed-plasmid DNA complex, the plasmid DNA has different twisted shapes depending on pH. Thus, gold nanoseed-plasmid DNA complexes having various twisted shapes can be prepared using buffer.

Figure 2:
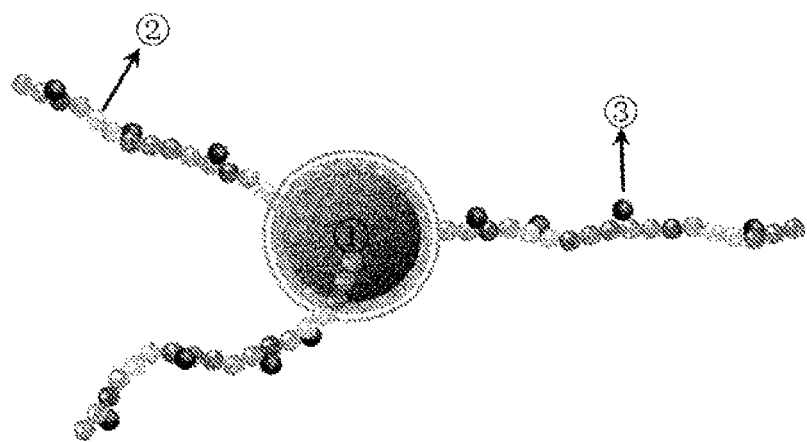
FIG. 2 is a schematic view showing metal ions deposited on a metal nanoseed-DNA complex.

To prepare a gold nanoseed-polypeptide complex, a magnetic particle is bound to a previously prepared polypeptide. The resulting magnetic particle-polypeptide complex is isolated by matrix-assisted laser desorption/ionization (MALDI) and fluorescence activated cell sorting (FACS). A gold nanoseed aqueous solution is added to the complex, followed by incubation. The cysteine thiol group of the polypeptide binds to the gold nanoseed to form a magnetic particle-polypeptide-gold nanoseed complex. FIG. 2 is a schematic view showing gold ions deposited on the surface of the nanoseed-polypeptide complex.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

(1) Oligonucleotides used in the present invention were purchased from Integrated DNA Technologies. Unless otherwise stated, other reagents were purchased from Sigma Aldrich. All chemical solutions and buffers were prepared in ultrapure water (18.2 mQ/cm).

(2) Gold nanostructures were observed using atomic force microscopy (AFM), scanning electron microscopy (SEM), transmission electron microscopy (TEM) and Fast Fourier Transform (FFT). The elementary analysis of nanostructures was performed by energy-dispersive X-ray spectroscopy (EDX). Crystal patterns were determined by X-ray crystallography (XRD). Growth thermodynamics was analyzed by UV-Vis-NIR spectroscopy. In addition, gold nanocluster growth processes were investigated by localized surface plasmon resonance (LSPR).

Preparation Example 1

Preparation of Aqueous Solution of Gold Nanoseeds

An aqueous solution of gold nanoseeds was synthesized by reducing $HAuCl_4$ with sodium citrate. Under intensive stirring, 20 mL of 0.25 mM $HAuCl_4$ solution was heated until boiling. Then, 2.0 mL of 5.0 mM sodium citrate solution was quickly added thereto, and a continuous color change from colorless to red was observed. When stirring was continued for 10 minutes, the color change was stopped. Next, the heating source was removed, and stirring was continued again for 15 minutes. When the solution was cooled to room temperature, distilled water was added to replace evaporated water. The final solution was filtered through a 0.2 μm membrane filter and stored at 4° C.

To introduce a carboxyl group onto the surface of pure gold, a self-assembled monomolecular layer terminated with oligo(ethylene glycol) was formed.

1.0 mL of an anhydrous ethanol solution containing $HS(CH_2)_{11}(OCH_2CH_2)_6OCH_2COOH$ ($OEG_6$-COOH, ProChimia) and $HS(CH_2)_{11}(OCH_2CH_2)_3OH$ ($OEG_3$-OH, ProChimia) at a molar ratio of 1:9 was added to 9.0 mL of a gold nanoparticle solution to a final concentration of 0.5 mM. The mixture was incubated overnight at room temperature with gentle stirring to form mixed SAM on the gold surface. Then, the mixture was centrifuged (14000 rpm, 30 min, 4° C.), and the supernatant was decanted, after which the pellets were washed with PBS buffer (0.01 M, pH 6.0). This centrifugation/resuspension procedure was repeated three times or more to remove ethanol and unattached OEG molecules, thereby preparing an aqueous solution of carboxyl-stabilized gold nanoseeds.

Example 1

(1) Preparation of Gold Nanoseed-DNA Complex

A complex of a gold nanoseed and a double-stranded DNA having 50 or less nucleotides was prepared by a one-after-another approach. A first DNA was bound to a gold nanoseed, and then second and third DNAs were sequentially bound thereto.

Figure 1:
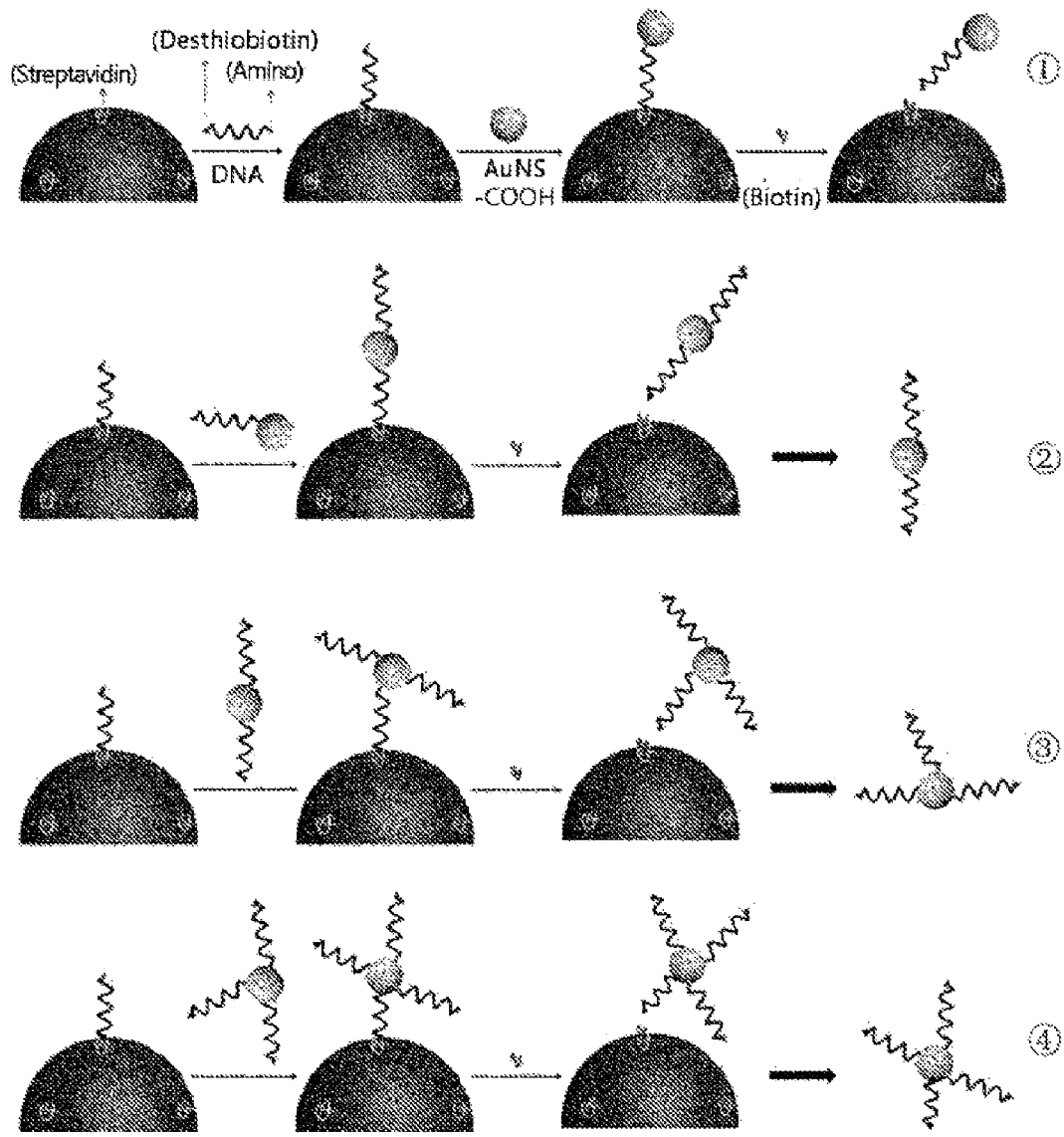
FIG. 1 is a schematic view showing a process of forming a metal nanoseed-DNA complex by a one-after-another approach.

FIG. 1 is a schematic view showing a process of forming the gold nanoseed-DNA complex.

0.6 mL of para-streptavidin-modified magnetic particles (PMPs) were mixed with 1.0 nmol of desthiobiotin-modified DNA, and the mixture was incubated at room temperature for 30 minutes with gentle shaking. To prevent non-specific binding, 0.5 mL of a blocking solution (0.01 M PBS buffer; 2%BSA and 5% PEG) was added. Then, the mixture was incubated again for 30 minutes and washed, and 0.1 M of 1-ethyl-3-(3-dimethylaminopropyl)carbodiimide (EDC) and 0.1 M of N-hydroxysuccinimide (NHS) were added thereto. Next, the gold nanoseed aqueous solution was added to the mixture, followed by incubation at room temperature for 4 hours with gentle shaking. Next, the solution was washed three times to removed unreacted gold nanoseeds.

Next, the solution was suspended in 1 mL of 1 uM biotin solution (pH 7.4). The suspension was incubated at room temperature for 3 hours with gentle shaking. DNA-bound gold nanoseeds and PMPs were magnetically separated from each other to obtain a gold nanoseed-DNA complex which was then stored at 4° C.

(2) Growth of Gold Ions on Surface of Gold Nanoseed-DNA Complex

The growth of gold ions was performed by the reduction of gold ions and the deposition of gold ions on the gold nanoseed-DNA complex. A growth solution was prepared using $HAuCl_4$ (hydrogen tetrachloroaurate(III)) as a gold ion source and hydroxylamine ($NH_2OH$) as a reducing agent.

Figure 4A:
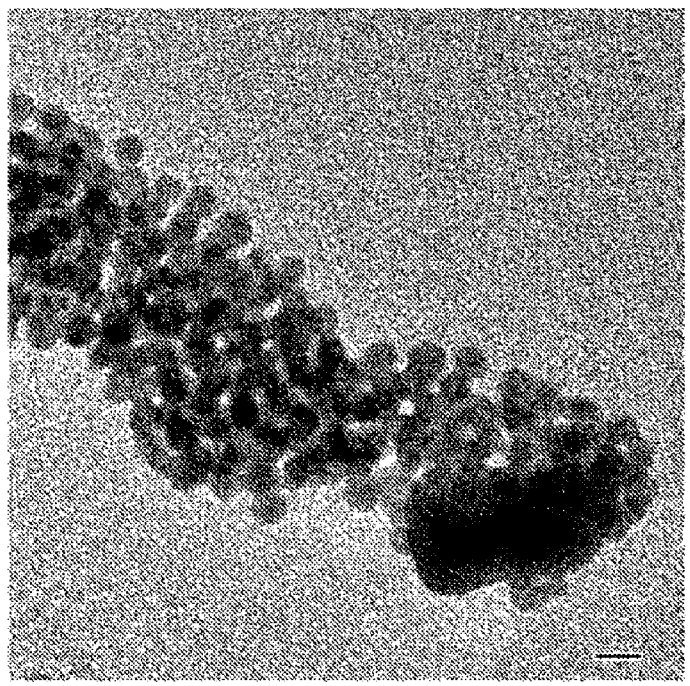
FIG. 4A is an HR-TEM image showing metal ions deposited on surface of metal nanoseed-DNA complex.
Figure 4B:
FIG. 4B is a photograph showing the change in color of growth solution by the deposition of metal ions on the surface of metal nanoseed-DNA.
Figure 5:
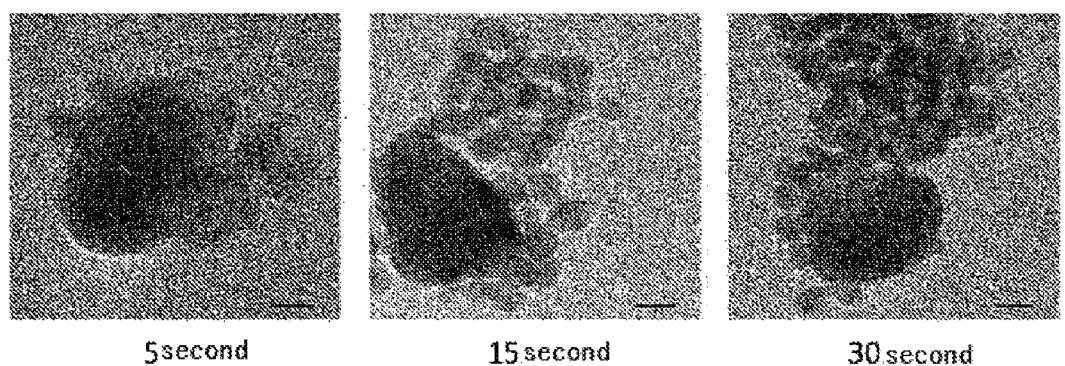
FIG. 5 is an HR-TEM image showing the binding between metal ions and MPA as a function of time.
Figure 10:
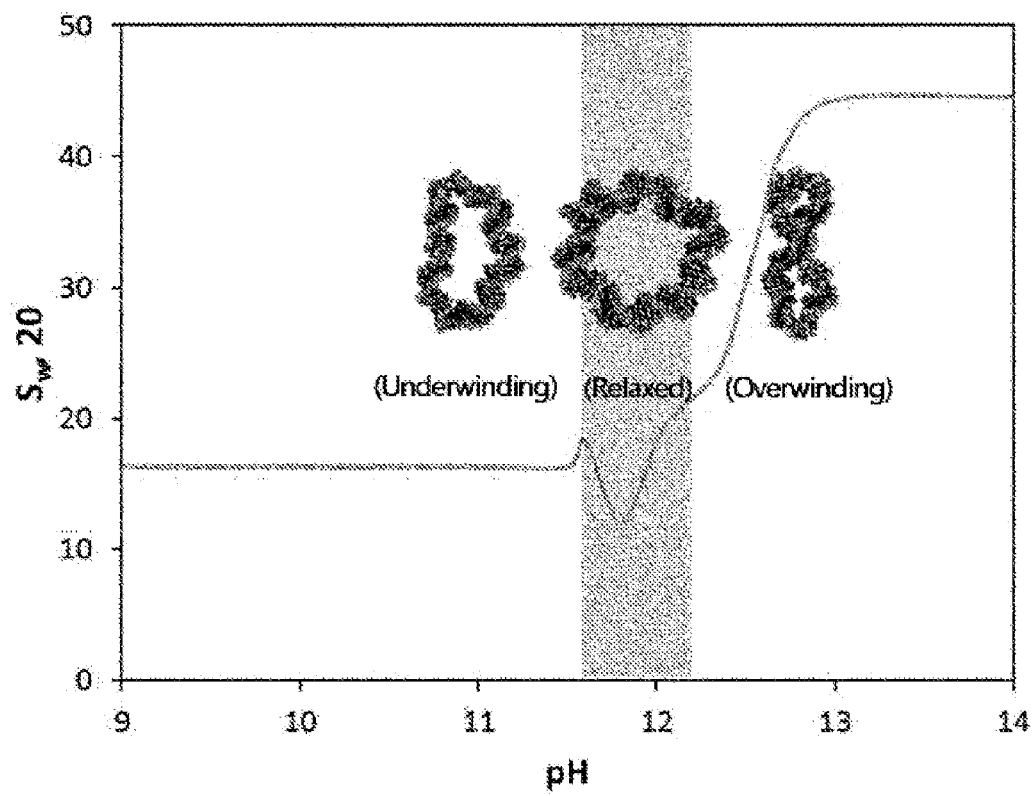
FIG. 10 depicts a graph showing the sedimentation coefficient of plasmid DNA as a function of pH, and a schematic view showing a change in the state of super-helices.

The growth solution was loaded with the gold nanoseed-DNA complex. As gold ions were deposited on the surface of the gold nanoseed-DNA complex, a visible change in the color of the growth solution occurred. FIG. 4A is an HR-TEM image showing gold ions deposited on the gold nanoseed-DNA complex, and FIG. 4B is a photograph showing the change in color of the growth solution during the deposition of gold ions on the gold nanoseed-DNA complex as a function of time.

(3) Termination of Gold Particle Growth

Mercaptopropionic acid (MPA) as a reaction terminating agent was added to inhibit further deposition. As can be seen in FIG. 4, as gold ions did bind to MPA, the fold ions were no longer deposited on the gold nanoseed-DNA complex, indicating that the growth of the gold ions was terminated.

FIG. 6 shows an HR-TEM image and schematic view of the nanostructures (nanostars) prepared in Example 1.

FIG. 7 is the X-ray diffraction spectrum of the gold nanostructures prepared in the Example; FIG. 7A is an HR-TEM image; and FIG. 7B is an FFT image.

FIG. 8 shows the energy-dispersive X-ray (EDX) spectrum of the prepared gold nanostructures. In FIG. 8, peaks at around 2 keV (M line) and 10 keV (L line) indicates gold nanostructures, and other peaks correspond copper, DNA and residue. Thus, it was confirmed that gold nanostructures were prepared according to the Example of the present invention.

Example 2

(1) Preparation of Gold Nanoseed-DNA Complex

A complex of a gold nanoseed and a double-stranded DNA having 50 or more nucleotides was prepared by a ligand exchange reaction between a mononucleotide and a DNA having a terminal disulfide group, followed by electrophoresis. As the mononucleotide, dATP was used, because dATP strongly bind to gold nanoparticles compared to other mononucleotides (dCTP, dGTP and dTTP) and shows strong salt resistance.

Deoxyadenosine triphosphate (dATP) and OEG-OH (HS($CH_2$)$_{11}$($OCH_2CH_2$)$_3$OH (ProChimia) were added to an aqueous solution of gold nanoparticles and incubated at room temperature. Thiol-terminated DNA was added to the incubated solution and stirred for 2 hours. 10 vol % (⅕ equivalents) of glycerol was added to the solution which was then loaded on 2% agarose gel. The gel was electrophoresed in 0.5× Tris-borate-EDTA buffer at a rate of 7 V/cm to remove unreacted material and dATP and separate a gold nanostructure-DNA complex. As can be seen in FIG. 3, the gold nanoseed-DNA complex formed a band on agarose gel depending on the number of DNAs bound to the gold nanoseed, indicating that it could be separated.

Steps (2) and (3) were performed in the same manner as described in Example 1.

FIG. 9 is a TEM image showing nanoflowers prepared according to Example 2.

Examples 3 to 5

(1) Preparation of Gold Nanoseed-DNA Complex

A gold nanoseed-DNA complex comprising a plasmid DNA was prepared using 1-pyrenebutyric acid (PBA) that is a DNA intercalating molecule.

A plasmid DNA (pUCI9) was isolated from *E. coli* and purified by cesium chloride gradient centrifugation in the presence of ethidium bromide.

The plasmid DNA was mixed with 10 nM PBA and stirred for 1 hour. The stirred mixture was desalted on an NAP column (GE Healthcare) to prepare 1 nM plasmid DNA solution. The plasmid DNA solution was activated by adding 0.1 M of 1-ethyl-3-(3-dimethylaminopropyl)carbodiimide (EDC) and 0.1 M of N-hydroxysuccinimide (NHS) thereto.

1.0 mL of an anhydrous ethanol solution containing OEG-OH and OEG-$NH_2$ ((HS($CH_2$)$_{11}$($OCH_2CH_2$)$_6$$OCH_2NH_2$) at a molar ratio of 10:1 was added to 9.0 mL of a gold nanoseed aqueous solution to a final concentration of 0.5 mM. The mixture solution was gently shaken at room temperature for 6 hours to form pellets, followed by washing to remove unreacted material. The pellets were suspended in 10 mM PBS buffer (pH 7.4) and mixed with the activated plasmid solution. The mixture was stirred for 3 hours, and then centrifuged at 4° C. and 14000 rpm for 30 minutes for 30 minutes. The supernatant was removed, and the remaining material was washed with Tris buffer (0.01 M, pH 11, 12 or 13).

Steps (2) and (3) were performed in the same manner as described in Example 1.

Figure 11A:
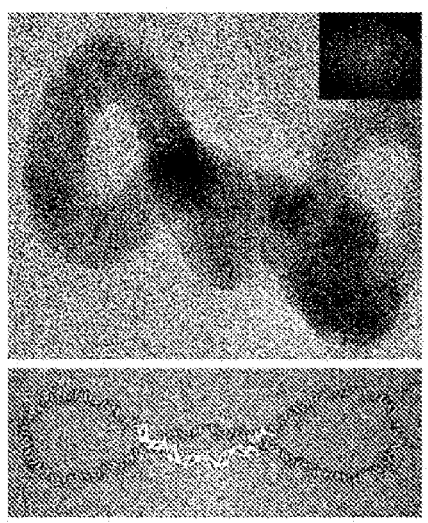
FIG. 11A is an HR-TEM image of nanocoils according to an embodiment of the present invention.
Figure 11B:
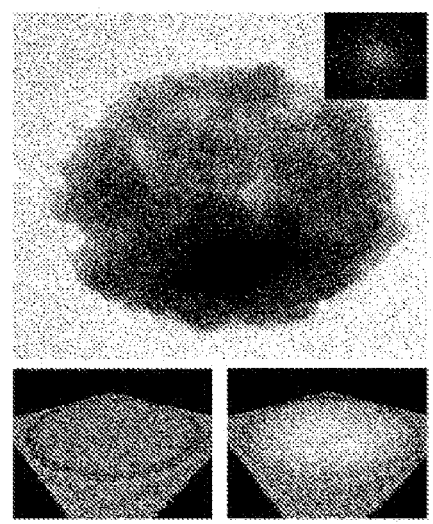
FIG. 11B is an HR-TEM image of nanodisks according to an embodiment of the present invention.

FIG. 11A is an HR-TEM image of nanocoils prepared using the plasmid DNA, and FIG. 11B is an HR-TEM image of nanodisks prepared using the plasmid DNA.

Measurement Example 1

The intensities of localized surface plasmon resonance (LSPR) of gold nanoseeds and the gold nanostructures prepared in Examples 1 and 2 were measured from Rayleigh scattering spectra using a dark-field microscope. To obtain Rayleigh scattering spectra, the dark-field microscope was collected with a spectrophotometer (Microspec 2300i, Roper Scientifics) and a high-sensitivity CCD camera (PIXIS: 400B, Princeton Instruments). First, gold nanorods were attached to a thiol-coated glass slide. Then, the glass slide was placed in a closed bath imaging chamber (RC-30, Warner Instruments, USA). The chamber was mounted on the sample holder of a dark-field microscope and connected with a syringe pump (Harvard Apparatus). An LSPR system was assembled, and then solutions containing distilled water and 20, 40, 60 and 80% glycerol were sequentially injected onto running cells, and Rayleigh scattering spectra from the gold nanorods were recorded. The Lorentzian algorithm was applied to fit the spectra, and OriginPro 7.5 software was used to provide accurate peaks and remove noise. The LSPR sensitivity of the nanosensors by the refractive index (RI)

change of the nanoparticle medium was determined by the refractive index (RI) change versus the LSPR maximum shift (unit: nm/RIU, RIU: refractive index).

Figure 12:
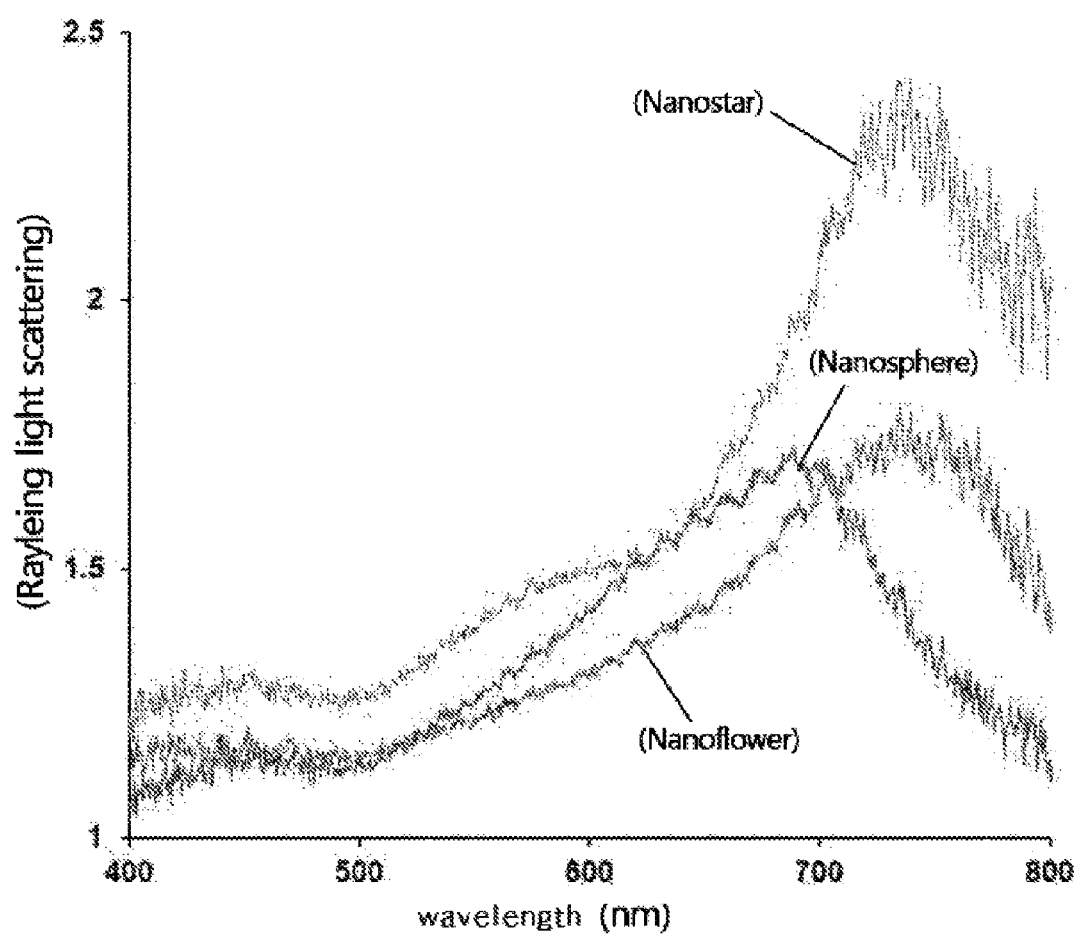
FIG. 12 is a graph showing the intensities of the localized surface plasmon resonance (LSPR) of metal nanoseeds and the metal nanostructures prepared in Examples 1 and 2.

The measurement results are shown in FIG. 12. As can be seen in FIG. 12, the intensity of localized surface plasmon resonance of the gold nanostructures according to the present invention was higher than that of gold nanoseeds. This indicates that the gold nanostructures according to the present invention can be advantageously used for fluorescent sensors and the like.

INDUSTRIAL APPLICABILITY

As described above, the method for preparing metal nanostructures according to the present invention is based on the self-assembly of biomolecules without using a surfactant, and enables the shape and size of the nanostructures to be easily controlled from the initial stage of the preparation process.

In addition, the metal nanostructures prepared by the method of the present invention can be widely used along with PDA liposomes in drug carriers, fluorescent sensing, drug delivery, biomedical imaging, supersensitive biosensors, etc.

The invention claimed is:

1. A method for preparing a biomolecule-based metal nanostructure, the method comprising the steps of:
   (a) forming a self-assembled monomolecular layer of a biomolecule on the surface of a metal nanoseed, thereby forming a metal nanoseed-biomolecule complex; and
   (b) growing a metal ion on the surface of the complex while reducing the metal ion with a reducing agent, wherein the metal nanoseed-biomolecule complex is prepared by the steps of:
      (i) binding a desthiobiotin-modified DNA to a streptavidin-modified magnetic particle to form a magnetic particle-DNA complex;
      (ii) binding the metal nanoseed to the DNA of the complex to form a magnetic particle-DNA-metal nanoseed complex; and
      (iii) adding a biotin solution to the magnetic particle-DNA-metal nanoseed complex to separate the bond between the magnetic particle and the DNA and remove the magnetic particle from the complex, thereby obtaining a metal nanoseed-DNA complex, wherein steps (i) to (iii) are repeatedly performed.

2. The method of claim 1, wherein step (i) further comprises, after forming the magnetic particle-DNA complex, a step of adding the magnetic particle-DNA complex to a mixture solution of EDC and NHS to activate the DNA.

3. A method for preparing a biomolecule-based metal nanostructure, the method comprising the steps of:
   (a) forming a self-assembled monomolecular layer of a biomolecule on the surface of a metal nanoseed, thereby forming a metal nanoseed-biomolecule complex; and
   (b) growing a metal ion on the surface of the complex while reducing the metal ion with a reducing agent, wherein the metal nanoseed-biomolecule complex is prepared by the steps of:
      (i) treating the metal nanoseed surface with a dATP having a terminal disulfide group and an oligo(ethylene glycol) (OEG-OH) having a hydroxyl group to form a self-assembled monomolecular layer, thereby modifying the metal nanoseed surface;
      (ii) adding a thiol-terminated DNA to the metal nanoseed, and separating and removing the dATP from the metal nanoseed by a ligand exchange reaction, thereby preparing a metal nanoseed-DNA complex; and
      (iii) recovering the metal nanoseed-DNA complex by electrophoresis.

4. A method for preparing a biomolecule-based metal nanostructure, the method comprising the steps of:
   (a) forming a self-assembled monomolecular layer of a biomolecule on the surface of a metal nanoseed, thereby forming a metal nanoseed-biomolecule complex; and
   (b) growing a metal ion on the surface of the complex while reducing the metal ion with a reducing agent, wherein the metal nanoseed-biomolecule complex is prepared by the steps of:
      (i) inserting a DNA intercalating molecule into a plasmid DNA, followed by desalting to obtain a plasmid DNA solution;
      (ii) adding a metal nanoseed aqueous solution to the plasmid DNA solution to form a metal nanoseed-plasmid DNA complex; and
      (iii) treating the metal nanoseed- plasmid DNA complex with a buffer (pH 10-14).

5. The method of claim 4, wherein the DNA intercalating molecule is 1-pyrenebutyric acid (PBA) or S-(2-[[4-(2-phenanthryl)butyl]amino]ethyl)hydrogen sulfurothioate).

6. The method of any one of claims 1, 3, and 4, wherein the source of the metal ion is one selected from the group consisting of hydrogen tetrachloroaurate(III) ($HAuCl_4$), sodium tetrachloroaurate(III) ($NaAuCl_4$), gold(III) chloride ($AuCl_3$), and potassium gold(III) chloride ($KAuCl_4$).

7. The method of any one of claims 1, 3, and 4, wherein the reducing agent is one selected from the group consisting of hydroxylamine ($NH_2OH$), sodium diphenylamine sulfonate, ascorbic acid, and poly(allylamine) hydrochloride.

8. The method of any one of claims 1, 3, and 4, wherein the method further comprises, after step (b), a step of adding mercaptopropionic acid to the complex to terminate the growth.

9. The method of any one of claims 1, 3, and 4, wherein the metal nanoseed is any one selected from the group consisting of nanospheres, nanorods, nanoprisms and nanosheets, and has a size of 1-100 nm.

10. The method of any one of claims 1, 3, and 4, wherein the metal nanoseed is made of any one selected from the group consisting of gold (Au), silver (Ag), platinum (Pt), palladium (Pd), copper (Cu), silicon (Si), germanium (Ge), aluminum (Al), and metal oxides.

11. The method of any one of claims 1, 3, and 4, wherein the biomolecule is any one selected from the group consisting of single-stranded DNAs, double-stranded DNAs, DNA oligomers, RNA oligomers, plasmid DNAs, polypeptides, and proteins, in which the single-stranded DNAs, the double-stranded DNAs, the DNA oligomers and the RNA oligomers are 5-5,000 bp in length, and the plasmid DNAs are 800-10,000 bp in length.

* * * * *